(12) United States Patent
Shirai

(10) Patent No.: US 11,454,577 B2
(45) Date of Patent: Sep. 27, 2022

(54) METHOD AND APPARATUS FOR COLLECTING BIOMOLECULES FROM SPECIFIC REGION OF TISSUE SECTION

(71) Applicant: HITACHI, LTD., Tokyo (JP)

(72) Inventor: Masataka Shirai, Tokyo (JP)

(73) Assignee: HITACHI, LTD., Tokyo (JP)

( * ) Notice: Subject to any disclaimer, the term of this patent is extended or adjusted under 35 U.S.C. 154(b) by 385 days.

(21) Appl. No.: 16/759,914

(22) PCT Filed: Oct. 3, 2018

(86) PCT No.: PCT/JP2018/036964
§ 371 (c)(1),
(2) Date: Apr. 28, 2020

(87) PCT Pub. No.: WO2019/097873
PCT Pub. Date: May 23, 2019

(65) Prior Publication Data
US 2021/0181076 A1 Jun. 17, 2021

(30) Foreign Application Priority Data
Nov. 17, 2017 (JP) .............................. JP2017-221689

(51) Int. Cl.
*G01N 33/53* (2006.01)
*G01N 1/31* (2006.01)
(Continued)

(52) U.S. Cl.
CPC ........... *G01N 1/312* (2013.01); *C12M 1/3407* (2013.01); *C12M 33/00* (2013.01); *G01N 1/04* (2013.01);
(Continued)

(58) Field of Classification Search
CPC ... C12N 15/1003; C12M 1/26; C12M 1/3407; C12M 1/42; C12M 33/00; C12Q 1/6844;
(Continued)

(56) References Cited

U.S. PATENT DOCUMENTS

| 8,588,502 B2* | 11/2013 | Nakano | G01N 15/1459 382/128 |
| 8,704,196 B2* | 4/2014 | Wolleschensky | G02B 21/0076 250/458.1 |

(Continued)

FOREIGN PATENT DOCUMENTS

| JP | 2003-130866 A | 5/2003 |
| JP | 2006-101718 A | 4/2006 |

(Continued)

OTHER PUBLICATIONS

Schermelleh, L.; Thalhammer, S.; Heckl, W.; Pösl, H.; Cremer, T.; Schütze, K.; Cremer, M. "Laser Microdissection and Laser Pressure Catapulting for the Generation of Chromosome-Specific Paint Probes", Ludwig Maximilians Universität, Munich, Academic Hospital München-Harlaching, Munich, Germany; BioTechniques vol. 27, No. 2, pp. 362-367, 1999.

(Continued)

*Primary Examiner* — Anh T Vo
(74) *Attorney, Agent, or Firm* — Volpe Koenig

(57) ABSTRACT

Provided is, in a sample of a cell or a micro region at a position designated in a microscope image of a tissue section, an apparatus and a method for analyzing a biomolecule, which are capable of collecting and analyzing a biomolecule in a single cell or in a micro region without damaging surrounding cells.

15 Claims, 7 Drawing Sheets

(51) Int. Cl.
*G01N 1/04* (2006.01)
*C12M 1/34* (2006.01)
*C12M 1/26* (2006.01)

(52) U.S. Cl.
CPC ... *G01N 33/5308* (2013.01); *G01N 2001/045* (2013.01)

(58) Field of Classification Search
CPC ...... G01N 1/04; G01N 1/312; G01N 33/5308; G01N 2001/045
See application file for complete search history.

(56) References Cited

U.S. PATENT DOCUMENTS

| | | |
|---|---|---|
| 2003/0081209 A1 | 5/2003 | Takahashi et al. |
| 2004/0001196 A1* | 1/2004 | Shibazaki .......... G01N 21/6428 356/129 |
| 2017/0016814 A1 | 1/2017 | Shirai et al. |

FOREIGN PATENT DOCUMENTS

| | | |
|---|---|---|
| WO | 9713838 A1 | 4/1997 |
| WO | 2015-097858 A1 | 7/2015 |

OTHER PUBLICATIONS

International Search Report and English Translation, PCT/JP2018/036964 dated Jan. 8, 2019, 4 pgs.

* cited by examiner

METHOD AND APPARATUS FOR COLLECTING BIOMOLECULES FROM SPECIFIC REGION OF TISSUE SECTION

TECHNICAL FIELD

The present invention relates to a method and an apparatus for selectively collecting, recovering, and extracting biomolecules (particularly, nucleic acids) from a specific region of a tissue section. In particular, the present invention relates to a method and an apparatus for individually collecting, recovering, and extracting nucleic acids from a single cell at a position corresponding to a microscope image.

BACKGROUND ART

In recent years, the importance of single-cell analysis that performs analysis with focusing on differences in the genome, gene expression, and protein of individual cells has been recognized when genomic analysis, gene expression analysis, and protein analysis of biological tissue including a large number of cells are performed.

In the single cell analysis, generally, disruption of binding between cells using chemical treatment such as trypsin treatment on cell clusters obtained from biological tissue allows cells to be isolated. However, since the cells in the tissue are dissociated, it is not possible to associate the cells on the optical image obtained by a microscope before isolation with the isolated cells. In other words, the positions of the cells in the tissue cannot be made to correspond to the single cell analysis result. In addition, it has also been a major matter of concern that the state of the cells, that is, the gene expression level, the protein level, and the like, may be altered by the chemical treatment for isolation.

On the other hand, as techniques of cutting out a micro sample from a specific position corresponding to the microscope image of a tissue section used for pathological diagnosis or the like and collecting the sample, techniques referred to as laser microdissection or laser capture microdissection as described in NPL 1 have been known. The techniques use the pressure and heat of laser light to cut out and collect a sample in a specific region. The collected sample is placed in a resin container or the like, and thereafter sample treatment for normal gene analysis or protein analysis is performed. However, in order to cut out a tissue section having a thickness of at least the cell size or larger by irradiation with laser light, a cutting margin of several μm or more is required. Since the cutting margin of several μm has about the same size as that of a cell, it has been difficult to isolate a single cell without damaging the cells in close proximity when cells are in close proximity to each other. In addition, there has also been a problem that damaging the surrounding cells causes the biomolecules contained in the surrounding cells to be mixed into the sample solution and the measurement accuracy to be reduced. Furthermore, isolation of cells from a section including a plurality of layers has been difficult because the conventional technique is a technique for cutting in a two-dimensional plane.

In addition, as another technique capable of collecting a sample at a specific position on a microscope image from a tissue section, there is a technique described in PTL 1. This technique uses a probe containing a selectively activatable adhesive with chemical adsorbing property or electrostatic adsorbing property rather than a laser in order to cut out and collect a sample in a specific region. However, since the shape of the probe containing the selectively activatable adhesive is difficult to fit to individual cells even with this technique, there is a problem that this technique affects surrounding cells at the time of collecting single cells.

Furthermore, PTL 2 describes an example in which cells are disrupted by a laser, and the cells are recovered in droplets before disruption. In order to recover cells from tissue sections, it is necessary to use laser microdissection (NPL 1) as described above, or dissociate cells by trypsin treatment or the like.

CITATION LIST

Patent Literature

PTL 1: WO 97/13838 A
PTL 2: JP 2006-101718 A

Non-Patent Literature

NPL 1: BioTechniques Vol. 27, No. 2, pp. 362-367, 1999

SUMMARY OF INVENTION

Technical Problem

As tissue sections for pathological diagnosis, two types of tissue sections are known, a tissue section created from resin-embedded samples such as formalin-fixed paraffin-embedded (FFPE) tissue samples and a tissue section created from samples without embedding and with or without freezing treatment or special treatment.

The present invention has an object to provide, in a sample of a cell or a micro region at a position designated in a microscope image of a tissue section, an apparatus and a method for analyzing biomolecules, which are capable of collecting and analyzing biomolecules in a single cell or in a micro sample without damaging surrounding cells.

Solution to Problem

In order to solve the above problems, the present invention provides an apparatus and a method for collecting, recovering, and/or extracting a biomolecule from a specific region of a tissue section by disrupting a specific region of a tissue section by applying energy, and collecting and recovering a biomolecule in the specific region in a droplet formed in contact with the specific region.

In one aspect, provided is an apparatus for collecting a biomolecule from a specific region of a tissue section, the apparatus including: a stage on which a tissue section is fixed; a microscope system configured to acquire an optical image of the tissue section; an energy application system configured to disrupt at least a part of a specific region of the tissue section; a dispensing pipette system configured to form a droplet on the tissue section; and a computer system configured to designate the specific region on the tissue section on an optical image acquired by the microscope system, wherein a biomolecule from the specific region being disrupted is dissolved or dispersed in the droplet.

In another aspect, provided is a method for collecting a biomolecule from a specific region of a tissue section, the method including: microscopically observing a tissue section; designating a specific region of the tissue section; dispensing a recovery solution on the tissue section so that a droplet to be formed covers the specific region, and forming a droplet; applying energy to at least a part of the specific region in a state where the droplet is present on the tissue section; and recovering the droplet.

Advantageous Effects of Invention

According to the present invention, a biomolecule present in a cell or a micro region at a designated position on a microscope image of a tissue section prepared from an FFPE section, a frozen section, or the like can be collected in a short time without damaging surrounding tissues. This makes it possible not only to collect a biomolecule with a surrounding tissue as another sample, but also to avoid contamination of a biomolecule from a region other than the designated region on the tissue section and to analyze a biomolecule from only the designated region. Problems, configurations, and effects other than those described above will be clarified by the following description of embodiments.

DESCRIPTION OF EMBODIMENTS

Figure 1:
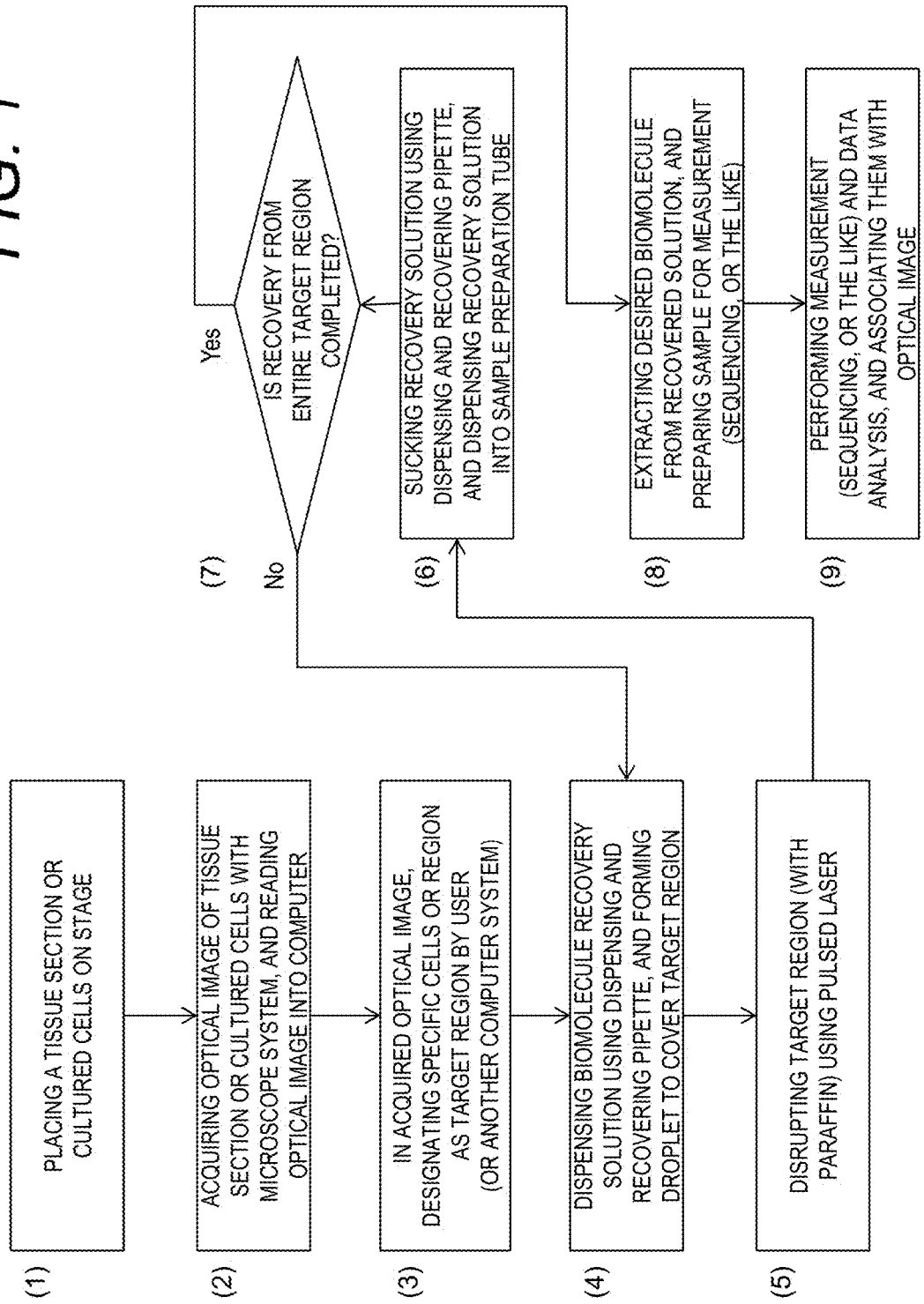
FIG. 1 is a flowchart of a method for collecting biomolecules according to an embodiment of the present invention.

Hereinafter, the present invention will be described in detail.

The present invention relates to an apparatus and a method for selectively collecting, recovering, and/or extracting a biomolecule from a micro region at a position corresponding to a microscope image on a tissue section. In particular, the present invention relates to an apparatus and a method for collecting, recovering, and/or extracting nucleic acids from a single cell individually at a position corresponding to a microscope image.

Here, "collecting" refers to taking out a specific region (specific cell or micro region) of a tissue section. "Collecting" or "recovering" refers to dissolving or suspending a biomolecule in the specific region in a solution and storing the biomolecule in a container. "Extracting" refers to preparing a solution in which a target biomolecule (such as only a nucleic acid) is concentrated.

According to the present invention, a specific cell (a single cell or a plurality of cells), or a specific micro region, for collecting a biomolecule is designated, and "micro" refers to a region having a diameter of about several tens of nm to several mm.

"Biomolecule" is not particularly limited as long as it is a biomolecule contained in a cell, and includes a nucleic acid (such as messenger RNA (mRNA), non-coding RNA (ncRNA), microRNA, genomic DNA, and fragments thereof), a protein (such as enzyme or antibody), and a low molecular weight compound. According to the present invention, one or more types of biomolecules may be collected, recovered, and/or extracted according to the purpose of analysis.

An apparatus for collecting a biomolecule of the present disclosure may include: a stage on which a tissue section (such as formalin-fixed paraffin-embedded (FFPE) tissue section or frozen section) is fixed; a microscope system, as a means for acquiring an optical image of the tissue section, and for designating a specific region on the tissue section (single cell or micro region) on the optical image; an energy application system as a means for disrupting at least a part of a specific region of the tissue section; a dispensing pipette system as a means for dispensing a recovery solution for dissolving or dispersing a biomolecule on the tissue section so that a droplet to be formed includes or covers a specific region, and forming a droplet; and a computer system for designating the specific region on the tissue section on an optical image acquired by the microscope system. A biomolecule from the disrupted specific region may be dissolved or dispersed in the droplet.

The stage is not particularly limited as long as the stage can fix a tissue section, a transparent plate to which the tissue section is attached, and a sample such as a cultured cell adhered onto a substrate. Preferably, the stage may be made of a transparent material (for example, FIG. 3) or the stage may be provided with a cutout region (for example, FIG. 4) so that observation with a microscope system can be performed. In addition, it may be preferable that the stage is provided with a fixture for fixing the sample, and this may allow the setting of the sample to be facilitated and the fixing position to be stabilized.

The microscope system is also not particularly limited as long as it is a means capable of acquiring an optical image (image data), and an optical microscope, an atmospheric pressure electron microscope, or the like can be used. In the optical image to be obtained, in order to determine and store information about the position and region on a sample such as a tissue section, the microscope system may be connected to a computer system.

The computer system may include components known in the technical field, and may be connected to other systems or components (such as a microscope system, a display unit, and an input unit) by wire or wirelessly. The computer system can perform designating a specific region (single cell or micro region) on a tissue section, recognizing a marker on a transparent plate as described below, and the like.

The energy application system is not particularly limited as long as it is a means capable of disrupting at least a part of a specific region of a tissue section. For example, it may include a light (laser light) irradiation system (such as a pulsed laser irradiation system), and a vibration generating device (such as an ultrasound application system).

Here, the disruption of a specific region (cell or micro region) of a tissue section by the energy application system refers to that applying light, vibration, heat, or the like to the region or the like allows a tissue section in this region to be broken down into micro fragments of several nm to several μm or less (along with the resin in some cases) and the fragments to be separated from the plate-shaped region forming the tissue section. As a result, a void may be formed in the corresponding region of the tissue section.

The dispensing pipette system is not particularly limited as long as it is a means capable of forming a droplet on a tissue section so as to include or cover a specific region. Specifically, a means may be used, which is capable of dispensing a recovery solution and forming a droplet on a tissue section with an appropriate amount and at an appropriate position so as to include or cover a specific region. Here, "forming a droplet on a tissue section" means that the droplet and the tissue section have only to be in direct or indirect contact with each other, and may include both forming a droplet in direct contact with a tissue section and forming a droplet via a water-repellent thin film present on a tissue section. It should be noted that preferably, the dispensing pipette system may also function as a means for recovering a droplet.

In one embodiment, the dispensing pipette system may include a mechanism to perform control so that the tip of the pipette keeps in contact with the droplet, whereby after a droplet is formed, the movement of the droplet can be controlled.

In another embodiment, the apparatus of the present disclosure may include: a needle-shaped component (such as a needle) for stabilizing a position of a droplet formed on the tissue section; and a mechanism configured to keep the needle-shaped component in a vicinity of a surface of the tissue section. This may allow the needle-shaped component to control the movement of a droplet after the droplet is formed on the tissue section.

In addition, a method for collecting a biomolecule of the present disclosure may include: microscopically observing a tissue section; designating a specific region (single cell or micro region) of the tissue section; dispensing a recovery solution for dissolving or dispersing a biomolecule on a tissue section so that a droplet to be formed includes or covers the specific region, and forming a droplet; applying energy (such as laser light irradiation or ultrasonic irradiation) to at least a part of the specific region in a state where the droplet is present on the tissue section; and recovering the droplet.

Furthermore, when the tissue section is a section having high hydrophilicity such as a frozen section, the above method may include applying a water-repellent thin film before or after observing the tissue section.

An apparatus and a method of the present disclosure may include: disrupting a cell or a micro region from which a biomolecule is to be collected, and collecting and recovering a biomolecule (such as a nucleic acid) fragmented and diffused by disruption into a droplet (recovery solution), rather than isolating all cells on a tissue section and collecting a biomolecule therefrom. Therefore, there is no cutting margin by laser microdissection. In addition, laser damage to the periphery of the selected cell can be reduced to a minimum. As a particularly desirable form, when the biomolecule to be collected is a hydrophilic molecule having an electric dipole, since the biomolecule dissolves in a droplet (recovery solution) at the same time as disrupting, the biomolecule may efficiently be recovered in a droplet (recovery solution) formed on the tissue section without the resin being chemically removed. It should be noted that even if the dissolution of the biomolecule in the droplet (recovery solution) at the same time as the disruption is not sufficient, since the resin fragment containing the biomolecule can also be recovered in the droplet (recovery solution), there is no difference in that the biomolecule can be efficiently recovered. In this case, chemical treatment (separation treatment with an organic solvent) for removing the resin may be necessary.

Furthermore, since it is possible not only to collect a cell sample of a specific micro region in a two-dimensional plane, but also to disrupt the section so as to have any shape in the thickness direction, it is also possible to collect a sample in the same shape.

A sample to which the method and apparatus of the present disclosure is applied may be a section embedded in a resin, a frozen section, a cultured cell (a cultured cell adhered onto a substrate), or the like. For example, when the method and apparatus of the present disclosure are applied to a formalin-fixed paraffin-embedded (FFPE) section, it is possible to form a droplet without including a step of applying a water-repellent thin film. This is because, in the case of a section embedded with a resin, when a droplet is formed, dissolution of the biomolecule in the tissue section in the droplet before disruption may be minimized. In the case of a frozen section or a cultured cell, forming a water-repellent thin film on the surface of the section in contact with the droplet may make it possible to prevent the diffusion and dissolution of the biomolecule into the droplet during the formation of the droplet. When handling these highly hydrophilic sections, it may be necessary to form a water-repellent thin film between the section and the droplet.

When the method and apparatus of the present disclosure are applied to a frozen section and a cultured cell, in one embodiment, a non-polar solvent can be used as the droplet (recovery solution). In another embodiment, the method of the present disclosure may include forming a water-repellent thin film on a frozen section, a cultured cell, or the like, and forming a droplet on the water-repellent thin film. In the apparatus of the present disclosure, such a frozen section or a section including a cultured cell and a water-repellent thin film disposed thereon may be used as a sample.

In a specific embodiment, a method for collecting a biomolecule of the present disclosure may be a method for collecting a biomolecule in a specific cell of a frozen section or an adherent cultured cell on a substrate, the method including: forming a water-repellent thin film on a frozen section or an adherent cultured cell on a substrate; microscopically observing the frozen section or the cultured cell; designating a specific cell of the frozen section or the cultured cell; dispensing a recovery solution on the water-repellent thin film so that a droplet to be formed covers the specific cell, and forming a droplet; applying energy to at least a part of the specific cell in a state where the droplet is present on the water-repellent thin film; and recovering the droplet.

In addition, for the purpose of facilitating buffer exchange to improve reaction efficiency after recovery, a step or means for capturing a biomolecule dispersed in a droplet by disrupting by applying energy to a specific region (single cell or micro region) on a nucleic acid probe dissolved in the droplet may be provided. That is, the droplet (recovery solution) may contain the nucleic acid probe. Alternatively, a step or means for capturing a biomolecule dispersed in a droplet on a bead suspended in the droplet may be provided. That is, the droplet (recovery solution) may contain a bead on which molecules that specifically bind to biomolecules are immobilized. For example, when the biomolecule is a nucleic acid (mRNA), a nucleic acid (DNA) probe containing a sequence complementary to at least a part of the sequence may be immobilized on a bead, and when the biomolecule is a protein or the like, an antibody that specifically binds to the protein may be immobilized on a bead.

The method and apparatus of the present disclosure may further include a step or means of collecting a biomolecule from a recovered droplet. In addition, the method and apparatus of the present disclosure may further include a step or means of collecting a biomolecule from the recovered droplet, and amplifying and sequencing the biomolecule.

Furthermore, in order to improve the reaction efficiency after recovery, the method and apparatus may include a step or means for performing a reaction such as degrading a biomolecule in a droplet.

Hereinafter, the present invention will be described in more detail with reference to embodiments, but the present invention is not limited to these embodiments.

First Embodiment

The present embodiment is an example relating to an apparatus and a method for disrupting a part of micro region in a tissue section made from a formalin-fixed paraffin-embedded (FFPE) sample by using a laser, and for collecting, recovering, and extracting biomolecules within the region.
(Method for Collecting and Recovering Biomolecules in Specific Region on Tissue Section)

FIG. 1 shows a flow of a method for collecting and recovering biomolecules from a tissue section shown in the present embodiment. In the following description, (number) indicates a number of each step in FIG. 1.

(1) First, a sample embedded in a resin such as FFPE may be sliced into a tissue section and placed on a stage. At this time, the tissue section may be attached and fixed to a transparent plate (a glass plate such as a slide glass or a cover glass, a transparent resin plate), and then the transparent plate may be placed on the stage. At this time, it may be desirable to adjust the position with respect to the stage by providing a marker for positioning on the transparent plate. Instead of cell sections, it is also possible to use frozen sections or cultured cells as described in the fourth embodiment.

(2) Next, an optical image (image data) of the tissue section may be acquired with the microscope system. In this step, the optical image may be shown to the user, and the user may designate a cell or a micro region from which biomolecules are to be collected. The number of cells or micro regions to be designated may be one or more. In addition, with regard to the optical image to be acquired, it may be desirable that staining such as hematoxylin-eosin (HE) staining or fluorescent immunostaining is performed as pre-treatment and the user can easily designate cells or regions to be collected on the tissue section. In the present embodiment, the fluorescent immunostaining method is adopted.

Therefore, a fluorescence microscope system is adopted as the microscope system. In the case of HE staining, a conventional optical microscope may be used. With regard to the microscope system, it may be desirable to adopt a required system according to the required resolution. Thereafter, the acquired optical image may be read into a computer.

(3) The user may designate cells or micro regions to be collected on the screen on which the microscope optical image of the tissue section is displayed, by using an input device such as a pointing device. The positional information on the designated cell or micro region may be calculated by the computer system, as the values on the coordinate axes set on the stage, and stored. Since the stored position coordinate information may be lost when the tissue section is removed or moved from the stage, the position of the cell or region has to be determined again using the microscope system. In order to eliminate such instability of the position coordinate information, it may be desirable to set alignment markers in at least two or more places on the transparent plate on which the tissue section is attached and fixed. Thus, when the transparent plate is set on the stage and the positional information on this alignment marker with respect to the stage coordinates is read, whereby even when the transparent plate is moved from the stage after the coordinates of the region to be collected are determined, re-reading the coordinates on the stage of the marker on the transparent plate may allow the position coordinates of the designated region with respect to the stage to be calculated, so that it is not necessary to determine the cell position again. In addition, as for the designation of cells or regions, in place of the user, the acquired image data may be transferred to another computer system and image analysis may be performed by this computer system, thereby designating cells or regions on the tissue section to be collected.

(4) When the user or the other computer system designates a plurality of cells or regions on a tissue section, the user or the other computer system may determine in which order of each cell or region to collect biomolecules therein. In order that droplets of the biomolecule recovery solution are formed in a manner of including or covering (one of) the cells or regions as a target region, the recovery solution may be dispensed by using a dispensing and recovering pipette system. Preferably, keeping the tip of the nozzle (tip) of dispensing of the pipette system in contact with droplets even after the dispensing is completed may prevent droplets from moving from the corresponding region on the tissue section without control by using surface tension.

(5) Irradiating at least a part of the target region with a certain energy using a pulsed laser may cause paraffin and biological tissue to be disrupted by the heat and pressure of the laser light, and the biomolecules within the tissue section to be collected in the droplets formed in step (4).

(6) The droplets after completing the collecting may be sucked by the dispensing and recovering pipette system, and the solution may be dispensed into a predetermined container (tube) and recovered.

(7) Steps (4), (5), and (6) may be repeated until recovering from all cells or micro regions designated in advance is completed.

(8) After an extracting step is performed as needed from the recovered solution, sample preparation necessary for measurement (sequencing, or the like) may be performed.

(9) Measurement (sequencing, or the like) and data analysis may be performed and be associated with the optical image (image data).

According to the present invention, performing the above steps makes it possible to perform analysis relating to biomolecules in each region or cell on a plurality of specific micro regions, preferably a plurality of single cells, on a tissue section. Even if the user designates a plurality of cells adjacent to a micro region or a single cell, in order to prevent contamination of biomolecules from other than designated cells or regions and reduction in recovery efficiency, the inside of the boundary line where the cells are adjacent to each other may be irradiated with a laser beam and a section in the designated portion may be disrupted. The laser light irradiation focuses the laser light so as to obtain an irradiation region as small as possible and scans regions or cells, whereby the designated regions or cells are disrupted. The laser to be used is not particularly limited as long as the section can be disrupted, examples thereof may include a pulsed laser and a continuous wave laser, and a pulsed laser is more desirable than a continuous wave laser. In particular, a pulsed laser with the order of picoseconds may be desirable. Since this reduces the average power of the laser light and increases the light energy per pulse, this can reduce the effect of heating the section by laser light irradiation, can enhance the effect of applying pressure by light and disrupt the section, and can increase the force of dispersing the irradiated portion. In the present embodiment, a pulsed laser having a pulse width of several picoseconds has been used.

Next, the recovery solution will be described. The recovery solution is classified into the following three types according to the treatment method after the recovery of biomolecules, that is, the measurement application. The first method is a method in which a sample dispersed from a tissue section is dispersed in a solution and recovered into a container by a dispensing and recovering pipette system. At this time, salt or a surfactant may be mixed in for the purpose of dispersing the resin constituting the tissue section such as paraffin. In addition, a surfactant may be mixed in order to prevent non-specific adsorption on the section surface or the inner wall of the pipette or the container (tube). In addition, as a method for extracting nucleic acids and proteins after recovering into a container (tube), a general extracting method can be used.

The second method is a method in which molecules that bind to biomolecules to be recovered is mixed into a recovery solution to recover the biomolecules stably and efficiently. Specifically, when the biomolecules to be recovered are mRNA, the magnetic beads on which the oligo dT probe is immobilized may be mixed with the recovery solution, and the mRNA may be bound to the oligo dT probe on the magnetic beads by hybridization. This solution may be recovered by a dispensing and recovering pipette system. In addition, in the case of a specific gene (mRNA) or non-coding RNA, a nucleic acid probe (DNA probe) having a sequence complementary to a part of a sequence of the gene or non-coding RNA may be immobilized on beads, and the RNA to be recovered on the beads may be captured in the droplet and recovered in an extraction solution. Furthermore, when the biomolecule is a protein, an antibody that specifically binds to the protein to be recovered may be immobilized on beads, and the target protein may be captured by the antibody and extracted in the solution. Before capturing biomolecules by this second method, biomolecules may be captured on the beads by adding protease and a surfactant for degrading molecules other than the molecules to be recovered in cells and tissues and irradiating with laser light, and then adding the solution containing the beads. In addition, when the beads are magnetic beads, extraction of biomolecules may become easier. That is, dispensing the recovery solution into a container (tube) and recovering the sample, then using a magnet to collect the beads at the bottom of the container, then removing the supernatant, and dispensing into the container a buffer solution suitable for biomolecules to be newly extracted may make it possible to remove molecules other than the biomolecules to be analyzed.

Lastly, the third method is a method including a reaction in a droplet between biomolecules and molecules in the droplet (recovery solution). For example, when the biomolecule to be recovered is a genomic DNA, as a recovery solution, a solution containing beads on which a DNA probe containing a restriction enzyme for DNA fragmentation and a random sequence of 6 to 8 base length is immobilized may be dispensed with a dispensing pipette. Thus, the fragmented DNA may be captured by the probe on the beads, and the genomic DNA can be extracted by a method similar to the second method. It should be noted that in this method, beads may not be necessarily required.

(Apparatus for Collecting Biomolecules from a Part of Region of Tissue Section (Using Pulsed Laser))

Figure 2:
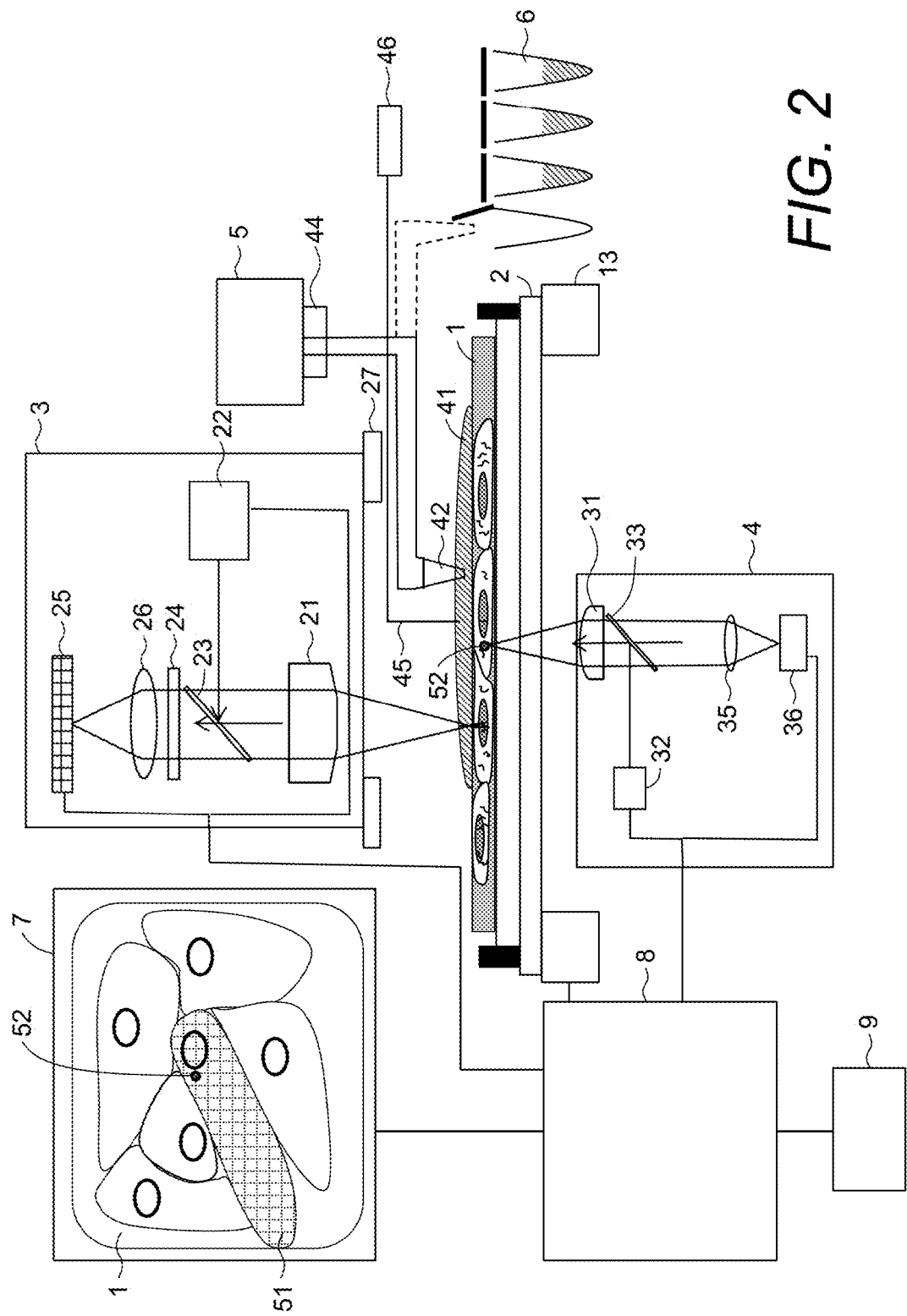
FIG. 2 is a configuration diagram of a biomolecule collecting apparatus according to a first embodiment of the present invention.

Next, an apparatus for collecting and recovering biomolecules from a plurality of single cells or regions on a tissue section will be described. FIG. 2 shows a configuration example of the apparatus. The apparatus includes: a stage 2 on which a resin-embedded tissue section 1 is fixed, a microscope system 3, a laser irradiation system 4, a dispensing pipette system 5, a solution recovery tube 6, a display device 7 for displaying a microscope image of a tissue section, a computer system 8 for controlling these systems, storing the acquired images, and converting the acquired images to positional information, and an input device 9 for inputting cells or regions to be collected into this computer system. Instead of this input device, another computer system for designating cells or regions may be connected to the computer system 8. Details will be described below.

Figure 3:
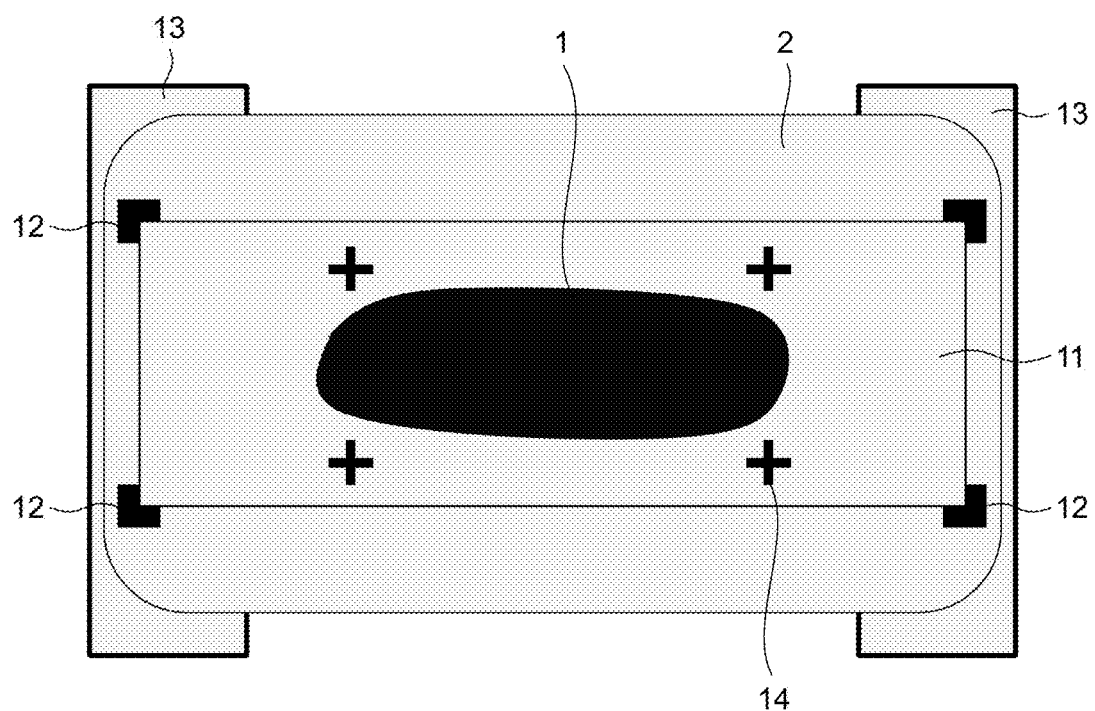
FIG. 3 is a top view of an example of a stage.

First, the periphery of the stage 2 will be described. FIG. 3 shows a top view of the stage 2. In the present embodiment, the tissue section (FFPE) is attached and fixed on a transparent glass plate 11, and the glass plate 11 is set on the stage 2. An L-shaped protrusion 12 for alignment is fixed on the stage 2, and setting the glass plate 11 in accordance with this allows alignment to be performed within the range of machining accuracy. The stage 2 is controlled by a computer system 8 for horizontal movement on the glass plate surface and movement perpendicular to the surface. The movement of the stage is performed by a triaxial motor drive stage 13. In addition, as described above, four markers 14 that can be checked by the microscope system are set on the glass plate 11, and the coordinates of the four markers are acquired by the microscope system after the glass plate is fixed. These coordinates are coordinates of the three axes relative to the stage 2. In addition, at the same time, the coordinates of the position of cells or micro regions to be collected on the tissue section are acquired as coordinates relative to the markers with respect to the stage. Even when once the glass plate 11 is removed and the position of the glass plate 11 with respect to the stage 2 is deviated, by measuring the coordinates of the markers on the glass plate with respect to the stage with a microscope system, the coordinates of the position of the designated region or cell with respect to the stage can be calculated using the relative coordinates of the designated region or cell with respect to the markers.

Figure 4:
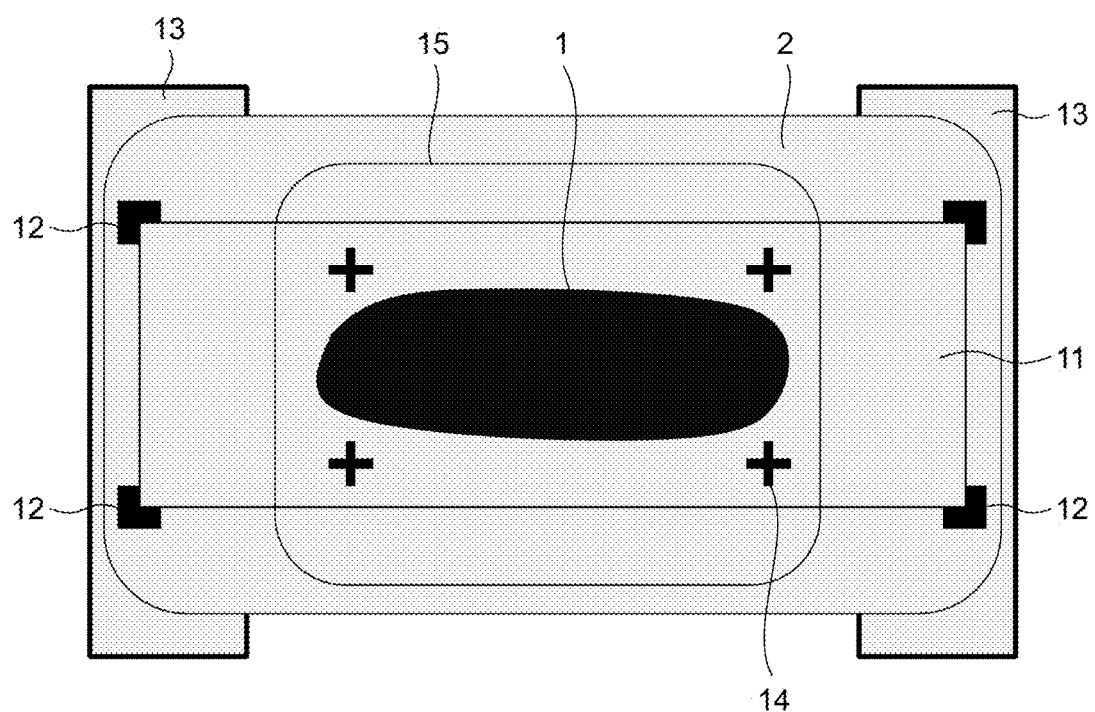
FIG. 4 is a top view of another example of a stage.

In addition, when an objective lens is used having a large numerical aperture and a small working distance in order to enhance the focusing capability by the objective lens of the laser irradiation system, the glass plate 11 is made to be thin, and the region of the stage 2, indicated by the reference numeral 15 in FIG. 4, is cut out so that the objective lens can be brought close to the vicinity of the back surface of the glass plate 11.

Although the microscope system 3 adopts a fluorescence microscope system in the present embodiment, various microscope systems such as a differential interference microscope, a phase contrast microscope, a laser excitation confocal fluorescence microscope, a Raman microscope, and an atmospheric pressure scanning electron microscope can also be used. The fluorescence microscope system 3 used in the present example includes: an objective lens 21, a laser for fluorescence excitation (wavelength 488 nm) 22, a dichroic mirror 23 for separating fluorescence and (scattered) laser excitation light by wavelength, a band-pass filter 24 for removing excitation light having passed through the dichroic mirror by wavelength and allowing only fluorescence to pass through, a CCD camera 25, and an imaging lens 26 for imaging fluorescent light on an image sensor of the camera. The imaging area of the camera can be moved with respect to the stage 2 by the motor drive stage 27.

The laser irradiation system 4 includes: an objective lens 31 for focusing laser light, a pulsed laser 32, a dichroic mirror 33 for separating laser light and fluorescence, an imaging lens 35, and an image sensor 36. Measuring the size of the fluorescence spot with the image sensor allows the state of focusing the laser light to be checked. A laser module having a pulsed laser whose wavelength is 532 nm, whose pulse width is about 10 psec, and whose pulse energy is variable from 1 pJ to 10 μJ has been used. Adjustment is made according to the size of the cell or region to be collected, the thickness of the section, the composition, and the like.

The dispensing pipette system 5 for dispensing and recovering the recovery solution is a system for dispensing the recovery solution 41 to an appropriate position, holding the formed droplet by using the surface tension at the tip of the chip during laser irradiation, thereafter recovering the droplet, and dispensing and recovering the droplet into appropriate containers 6. Since the FFPE sections have low hydrophilicity and large contact angles, it is possible to form a droplet that covers small regions, and at the time of droplet formation, highly hydrophilic nucleic acids and the like are less likely to dissolve. On the other hand, after disrupting by laser, the corresponding region is dispersed, and DNA and RNA among biomolecules are well soluble in water being a polar solvent, so that the biomolecules hydrate and stabilize in the recovery solution. In addition, even when nucleic acids are not eluted from the resin piece into the recovery solution, the presence of the surfactant in the recovery solution can prevent re-adsorption to tissue sections, and can efficiently recover biomolecules into the recovery solution. The pipette system 5 has a disposable chip (resin cone type dispensing cylinder) 42 attached to the tip of the pipette, moves the chip 42 to a bottle storing the recovery solution using the suction motor drive 44, and sucks the recovery solution from the bottle only by a predetermined amount. Next, a droplet is dispensed onto the tissue section so as to cover the cell or region designated in step (3). After dispensing, in order to prevent the droplet from moving on the tissue section, the height at which the tip of the chip 42 used for dispensing is in contact with the formed droplet is kept. After the disruption of the designated region or cell by laser is completed, the droplet on the tissue section is sucked into the pipette and discharged into the designated container 6. In addition, in the case where another type of solution is added after droplet dispensing, when a solution or a reagent is sucked from a solution bottle, sucking air after sucking the first solution, and further sucking the second solution prevents mixing of the first and second solutions. When a droplet is to be formed on a tissue section, the first solution is dispensed, and then after a predetermined process, the second solution is dispensed. When two or more types of solutions are to be dispensed, setting a needle 45 for stabilizing a droplet and a motor drive 46 for moving this needle in addition to the chip 42 allows the droplet to be stabilized even while the chip moves away from the droplet and moves into the reagent bottle. At this time, it is desirable that the tip of the droplet stabilizing needle has a hydrophilic surface.

A fluorescence microscope image of the tissue section 1 (the type of image also changes depending on the type of microscope) is displayed on a display device 7 connected to a computer system 8 for designating predetermined cells and regions on the tissue section. Here, the cell (or region) 51 from which biomolecules are desired to be collected is designated using the input device 9. A plurality of cells or regions on a section may be designated. On the computer, the range of the laser focus position 52 to be scanned is calculated from information on the position coordinates (range) on the stage of the region 51 and the position coordinates of the stage. The laser focus position scanning range uses parameters stored in advance in the computer system based on the size of the laser focus region and the like. For example, control may be performed so that the focus center scans a region about 0.3 μm inward from the designated range. For the laser focus position control, the stage may be controlled using the motor drive 13, but a galvano scanner may be set in the laser irradiation system to scan the focus position of the pulsed laser.

In addition, when a plurality of cells or regions are designated, the order in which biomolecules are collected (irradiated with laser light) can also be designated using the input device.

Second Embodiment

The present embodiment relates to an apparatus configuration when a plurality of dispensing chips on a dispensing and recovering pipette system are arranged.

Figure 5:
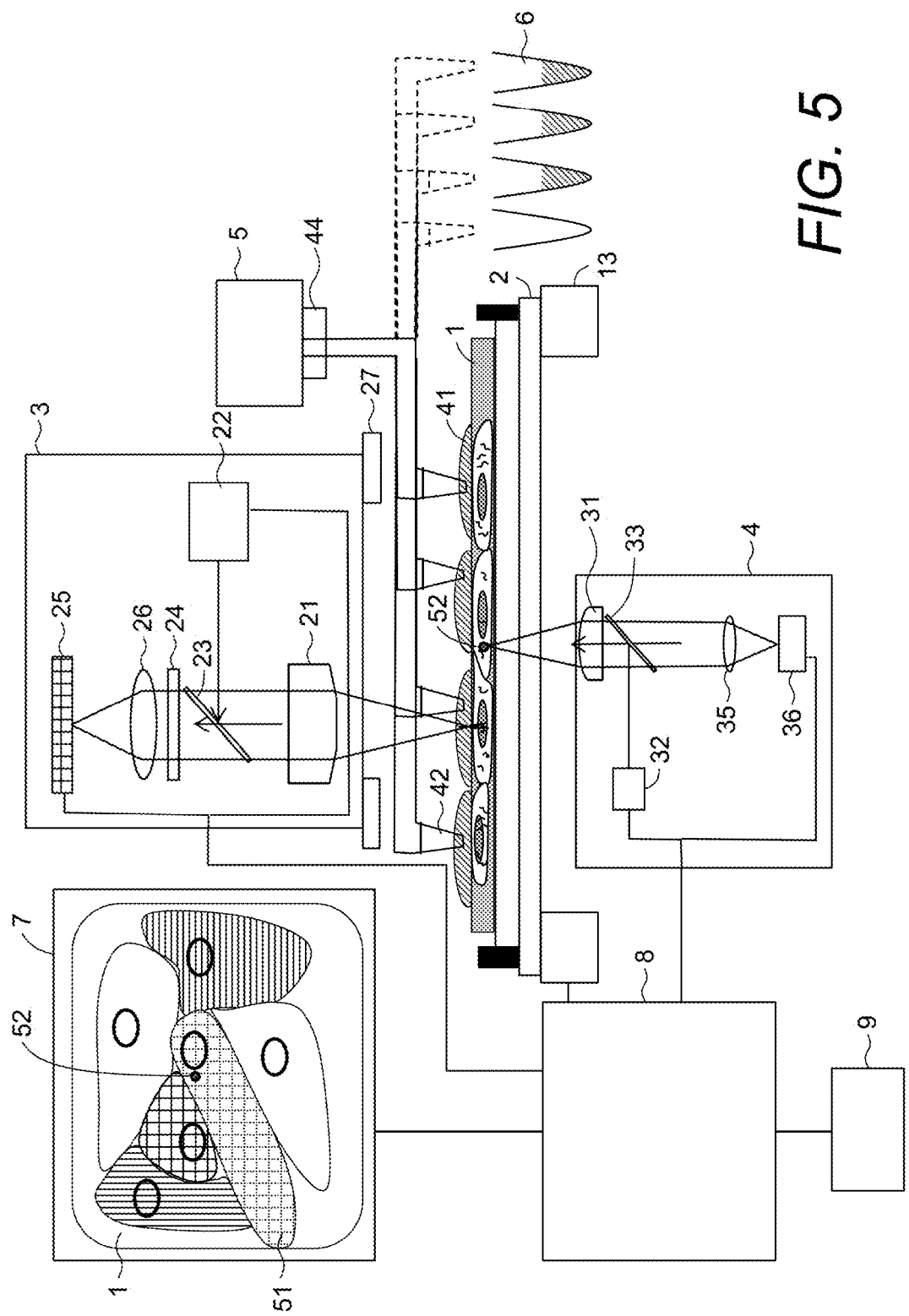
FIG. 5 is a configuration diagram of a biomolecule collecting apparatus according to a second embodiment of the present invention.

FIG. 5 shows an example of the apparatus. In this example, four chips 42 are mounted on the dispensing pipette system 5, and collection from four regions or cells can be performed in parallel. After the recovery solution is dispensed so that the designated four regions or cells on the tissue section are covered, a small amount of the recovery solution is dispensed so that these solutions are not mixed. When a tissue section is prepared, the resin surface desirably has low hydrophilicity (high water repellency).

Third Embodiment

Figure 6:
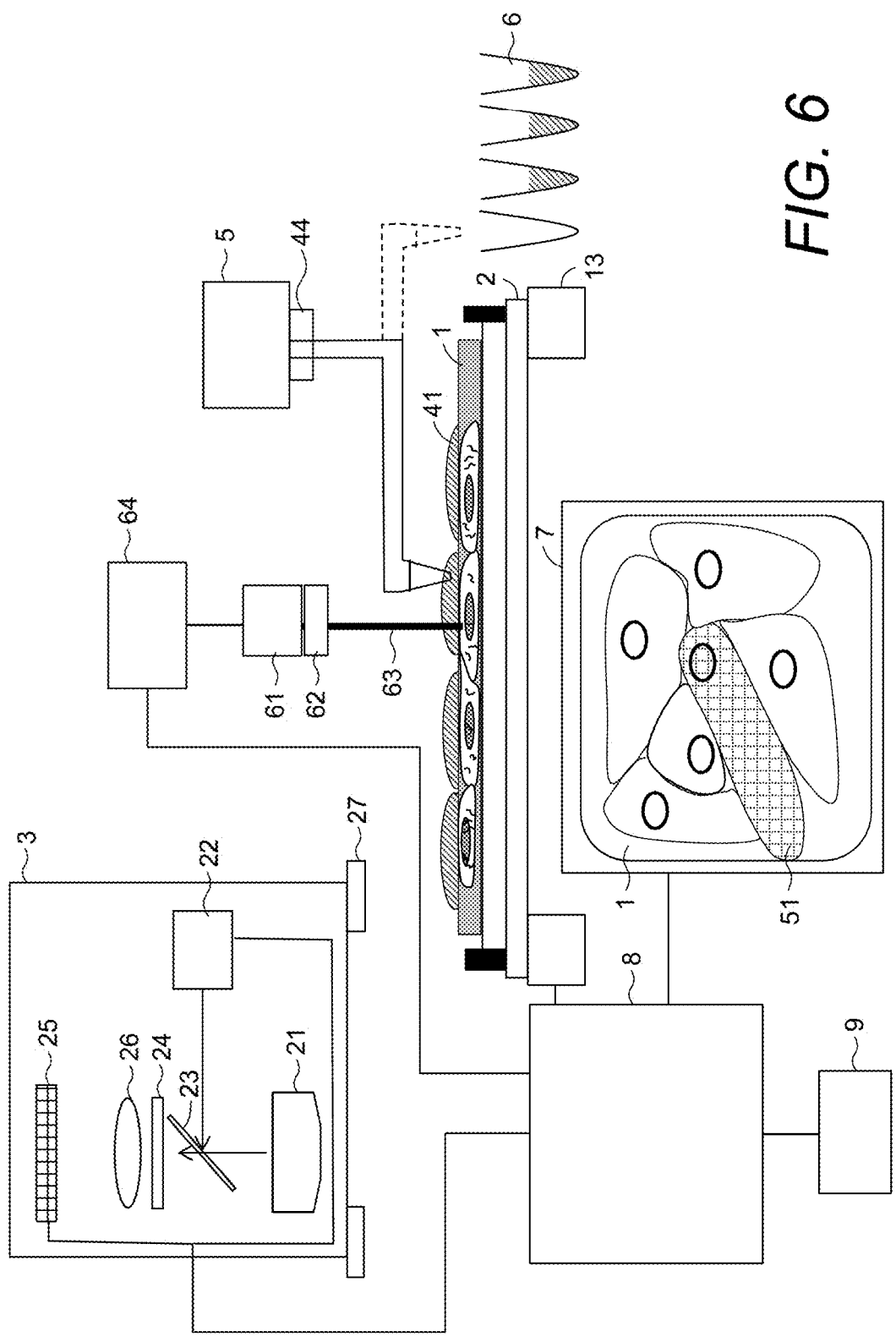
FIG. 6 is a configuration diagram of a biomolecule collecting apparatus according to a third embodiment of the present invention.

The present embodiment is an example in which a tissue section is disrupted using a vibration generating device (ultrasonic needle). Instead of the laser irradiation system in FIG. 2, as a vibration generating device, a system for applying ultrasonic waves to a specific position of a tissue section is set. FIG. 6 shows a configuration example of the apparatus. A piezoelectric needle (a high-hardness metal needle or a ceramic needle) 63 is fixed to the piezoelectric element 61, and a configuration in which ultrasonic vibration is transmitted to a part of a region in a specific region or cell of a tissue section is made. In order to apply ultrasonic waves to a specific region or cell, the application position of the needle is selected by the motor driver 62. In order to generate ultrasonic vibration, a high frequency generating device 64 for generating high frequency waves of a specific frequency is connected to a piezoelectric element (ultrasonic element). In the apparatus shown here, since the ultrasound application system has to be arranged on the same side as the microscope system with respect to the tissue section, an optical image is acquired using a microscope system, the region or cell from which biomolecules are to be collected is designated, and then the motor driver 62 is controlled using the computer system 8 so that ultrasonic waves are applied to the corresponding coordinates. Since using ultrasonic vibration allows the physical vibration to be transmitted directly to the tissue section, the tissue can be disrupted with minimal effect on the biomolecules.

Fourth Embodiment

The present embodiment is an example of collecting biomolecules from frozen sections and cultured cells on a petri dish based on the apparatus described in the first embodiment. It is also possible to perform a plurality of pieces of droplet formation as in the second embodiment, and it is also possible to concurrently use disruption using ultrasonic waves instead of laser as in the third embodiment.

Figure 7:
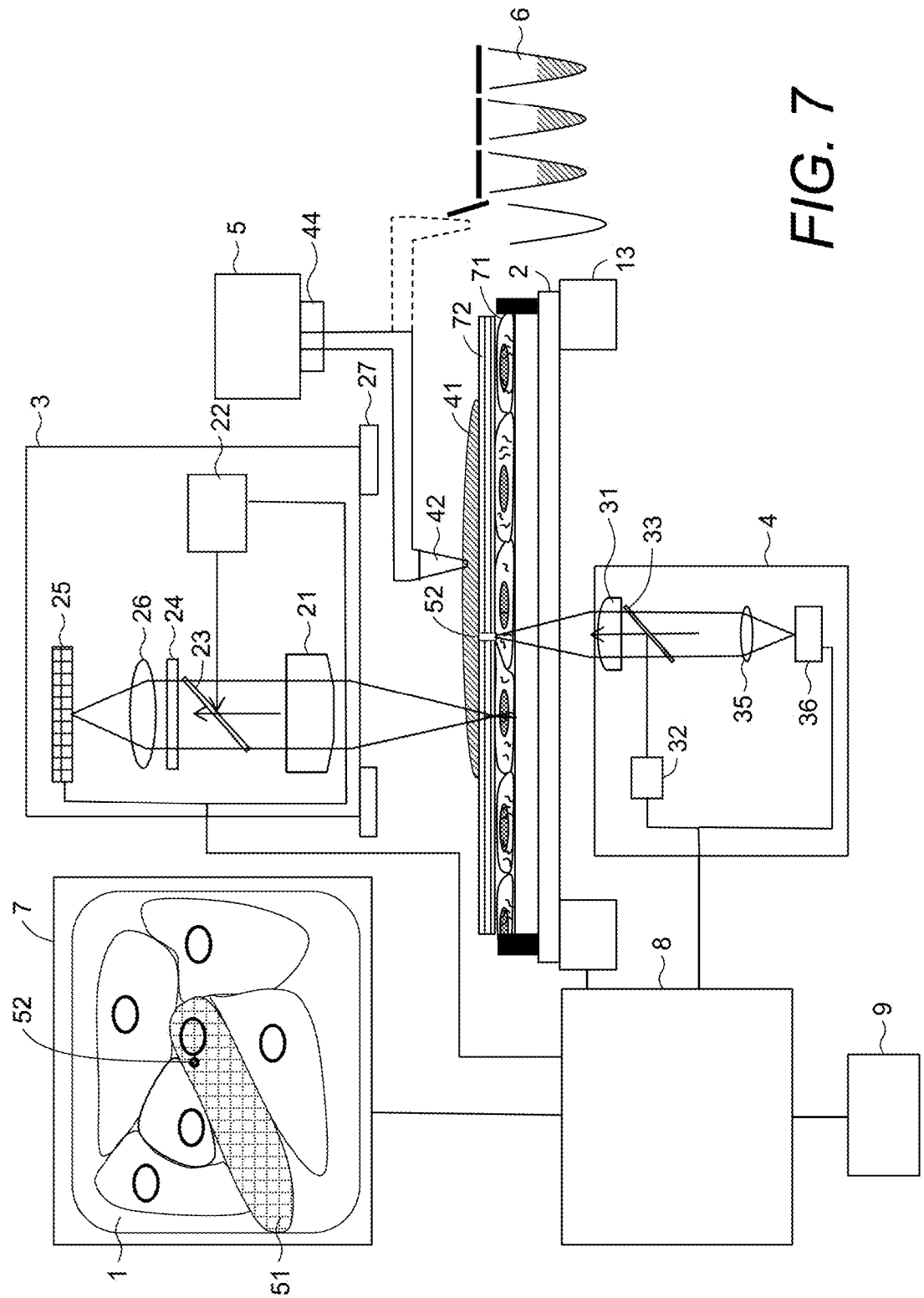
FIG. 7 is a configuration diagram of a biomolecule collecting apparatus according to a fourth embodiment of the present invention.

The difference between FFPE and frozen sections and cultured cells is that the sections are not embedded in a hydrophobic material. Therefore, droplets cannot be formed on frozen sections or cultured cells, and if partially disrupted cells are mixed in, there may arise a problem that the biomolecules in the disrupted cells are mixed into the droplets. In such cases, a water-repellent (or hydrophobic) thin film is formed on frozen sections or cultured cells. FIG. 7 shows an example of a system configuration diagram. This is almost the same as the configuration in FIG. 2, but the section is replaced with a frozen section 71 after drying from FFPE, and a water-repellent resin film 72 of 1 µm or less is applied thereon. When a section obtained by performing deparaffinization treatment on a FFPE section is used, it is necessary to apply a water-repellent thin film in the same manner as a frozen section. In the present embodiment, a silicone resin that is cured by UV irradiation is used. This resin is liquid before curing; and dripping on the frozen section 71, a water-repellent resin film is formed by performing a spin coating (for example, at 5000 rpm for 30 sec), forming a thin film of 0.3 µm in thickness, and irradiating with UV light (2 J/cm with 365 nm UV light). Examples of the silicone resin material may include UV curable PDMS or radical polymerization type silicone. When the latter is used, UV irradiation is performed in a nitrogen atmosphere.

The thickness of the thin film can be controlled by the viscosity in the solution state and the number of rotations during spin coating. The thickness of the thin film is desirably 0.05 µm to 10 µm. In particular, 0.2 µm to 0.5 µm is desirable.

The degree of water repellency of the water-repellent thin film is necessary to prevent the droplet from becoming too large when a droplet is formed, and is desirably 30 degrees or more and 180 degrees or less when evaluated by a contact angle. In particular, in controlling the droplet size, if the dispensing amount is small and the contact angle is about 70 degrees or more, it is possible to make the size (outer diameter) of the tip of the chip 42 in FIG. 7 almost the same as the droplet size to be dispensed, and it is possible to reduce the contact area between the droplet and the thin film. At this time, the distance between the tip (lower end) of the chip 42 and the water-repellent thin film surface is set to be about the same as the radius of the droplet.

In addition, the thin film needs to be transparent (transmit light of 5% or more) for microscopic observation. The wavelength of the transmitted light is the wavelength of the illumination, or the excitation laser, used in the microscope. The definition of water repellency is defined by a contact angle, and in the present invention, a combination of a thin film having a contact angle of 45 degrees or more (here, with regard to the definition of the contact angle, the contact angle in a state where the height of the droplet cannot be observed is 0 degree, and the contact angle is defined by the angle between the tangent along the boundary between the droplet and the air at the boundary between the droplet, the thin film, and the air, and the flat thin film top surface) and a solution is referred to as a water repellent film.

REFERENCE SIGNS LIST 1 tissue section
2 stage
3 microscope system
4 laser irradiation system
5 dispensing pipette system
6 solution recovery tube
7 display device
8 computer system
9 input device
21 objective lens
22 laser for fluorescence excitation
23 dichroic mirror
24 band-pass filter
25 CCD camera
26 imaging lens
27 motor drive stage
31 objective lens
32 pulsed laser
33 dichroic mirror
35 imaging lens
36 image sensor
41 recovery solution
42 chip
44 suction motor drive
45 stabilizing needle
46 motor drive
51 designated cell or region
52 laser focus position
11 glass plate
12 protrusion
13 motor drive stage
14 marker
15 cutout region
61 piezoelectric element
62 motor driver
63 piezoelectric needle
64 high frequency generating device
71 frozen section
72 water-repellent resin film

The invention claimed is:

1. An apparatus for collecting a biomolecule from a specific region of a tissue section, comprising:
    a stage on which a tissue section is fixed;
    a microscope system configured to acquire an optical image of the tissue section;
    an energy application system configured to disrupt at least a part of a specific region of the tissue section;
    a dispensing pipette system configured to form a droplet on the tissue section; and
    a computer system configured to designate the specific region on the tissue section on the optical image acquired by the microscope system,
    wherein a biomolecule from the specific region being disrupted is dissolved or dispersed in the droplet.

2. The apparatus according to claim 1, wherein the energy application system is a laser irradiation system comprising a pulsed laser, or a vibration generating device comprising a piezoelectric element.

3. The apparatus according to claim 1, further comprising:
    a needle-shaped component for stabilizing a position of a droplet formed on the tissue section; and
    a mechanism configured to keep the needle-shaped component in a vicinity of a surface of the tissue section.

4. The apparatus according to claim 1, wherein
    on the stage, a transparent plate to which the tissue section is attached is configured to be fixed, and
    the computer system comprises a mechanism configured to recognize a marker on the transparent plate.

5. The apparatus according to claim 1, wherein the specific region is a single cell or a micro region.

6. The apparatus according to claim 1, wherein the tissue section is a formalin-fixed paraffin-embedded (FFPE) section.

7. The apparatus according to claim 1, wherein the tissue section comprises a frozen section or a cultured cell, and a water-repellent thin film disposed on the frozen section or the cultured cell.

8. A method for collecting a biomolecule from a specific region of a tissue section, comprising:
    microscopically observing a tissue section;
    designating a specific region of the tissue section;
    dispensing a recovery solution on the tissue section so that a droplet to be formed covers the specific region, and forming a droplet;
    applying energy to at least a part of the specific region in a state where the droplet is present on the tissue section; and
    recovering the droplet.

9. The method according to claim 8, wherein applying energy comprises laser light irradiation or ultrasonic irradiation.

10. The method according to claim 8, wherein the droplet comprises a nucleic acid probe.

11. The method according to claim 8, wherein the droplet comprises a nucleic acid probe immobilized on a bead.

12. The method according to claim 8, wherein the droplet comprises an antibody immobilized on a bead.

13. The method according to claim 8, wherein the tissue section is a frozen section, and
    the method further comprising:
    forming a water-repellent thin film on the frozen section; and
    forming a droplet on the water-repellent thin film.

14. A method for collecting a biomolecule in a specific cell of a cultured cell adhered onto a substrate, comprising:
    forming a water-repellent thin film on a cultured cell adhered onto a substrate;
    microscopically observing the cultured cell;
    designating a specific cell of the cultured cell;
    dispensing a recovery solution on the water-repellent thin film so that a droplet to be formed covers the specific cell, and forming a droplet;
    applying energy to at least a part of the specific cell in a state where the droplet is present on the water-repellent thin film; and
    recovering the droplet.

15. The method according to claim 8, further comprising:
    collecting a biomolecule from the recovered droplet; and/or
    collecting a biomolecule from the recovered droplet, and amplifying and sequencing the biomolecule.

* * * * *